United States Patent [19]
Pandey et al.

[11] Patent Number: 5,591,847
[45] Date of Patent: Jan. 7, 1997

[54] LONG WAVELENGTH ABSORBING PHOTOSENSITIZERS RELATED TO PURPURIN-18, BACTERIOPURPURIN-18 AND RELATED COMPOUNDS WITH IMIDE LINKAGES

[75] Inventors: Ravindra K. Pandey, Williamsville; Thomas J. Dougherty, Grand Island, both of N.Y.; Kevin M. Smith, Davis, Calif.; Fuu-Yau Shiau, Sugar Land, Tex.

[73] Assignees: Health Research, Inc., Buffalo, N.Y.; The Regents of the University of California, Oakland, Calif.

[21] Appl. No.: 247,866

[22] Filed: May 23, 1994

[51] Int. Cl.⁶ .................................. C07D 487/22
[52] U.S. Cl. ................. 540/472; 540/145; 540/474
[58] Field of Search .................... 540/472, 145, 540/474

[56] References Cited

PUBLICATIONS

Lee et al., J. Chem. Soc. Perkin I (19) pp. 2369–2377; 1993.
Chang et al., J. Chem. Soc., Chem. Commun. pp. 1213–1215; 1986.

*Primary Examiner*—Mukund J. Shah
*Assistant Examiner*—Pavanaram K. Sripada
*Attorney, Agent, or Firm*—Michael L. Dunn

[57] ABSTRACT

Compounds having utility as light absorbing compounds, especially in the area of photodynamic therapy.

Such compounds have the formula:

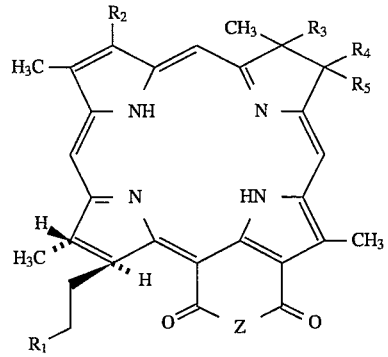

where Z is $=O$ or $=NR_6$, where $R_6$ is lower alkyl of from 1 to 8 carbon atoms or

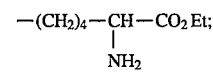

$R_1$ is

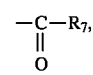

where $R_7$ is

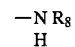

or $-OR_8$, where $R_8$ is hydrogen or lower alkyl of 1 to 8 carbon atoms, or $R_7$ is an amino acid residue connected at a nitrogen atom of such residue; $R_2$ is lower alkyl or lower alkylene of from 2 to 4 carbon atoms or a formal or carbonyl containing group of from 1 to 4 carbon atoms; $R_3$ and $R_4$ are $-H$ or $-OR_8$ or are joined together so that each represents one-half of a chemical bond and $R_4$ may be taken together with $R_5$ to form $=O$; and $R_5$ is ethyl or is taken together with $R_4$ to form $=O$; provided that when Z is $-O-$ the sum of the number of carbon atoms in $R_1$ through $R_5$ is from 12 to 20 and when Z is $=NR_6$, the sum of the number of carbon atoms in $R_1$ through $R_6$ is 8 to 20.

15 Claims, 9 Drawing Sheets

$R^7$ = methyl ester or asparticacid-di-*tert* butyl ester or other amino derivatives
$R^3$ = various alkyl groups
R = various amino acids or alkyl groups $R^7$ = methyl ester or asparticacid-di-*tert* butyl ester or other amino acids.
R = various amino acids or alkyl groups.

$R^7$ = methyl ester or asparticacid-di-*tert* - butyl ester or other amino acids.

LONG WAVELENGTH ABSORBING PHOTOSENSITIZERS RELATED TO PURPURIN-18, BACTERIOPURPURIN-18 AND RELATED COMPOUNDS WITH IMIDE LINKAGES

This work was supported by grants from the Oncologic Foundation of Buffalo, N.Y.

BACKGROUND OF THE INVENTION

Photosensitizers are chemicals which kill cells and/or fluoresce when activated by light of a specific wavelength. Most malignant and some premalignant tissues retain these photochemically active substances in higher concentrations and for longer durations than surrounding normal tissues. The retention time is not dependent on wether or not the cells are synthesizing DNA or cell growth or nutrient uptake. This form of treatment, therefore, is an important new part of cancer treatment and tumor detection (Dougherty, T. J., CRC Critical Rev. Oncol. Hematol., 1984, 83).

Photosensitizers have been recognized for almost a century. In 1900, (Rabb, C., Z. Biol., 1900, 39, 1423) reported the lethal effects of a combination of acridin orange dye and ordinary light on Paramecium. In 1903, von Tappeneir reported the first therapeutic use of photosensitizers when he used eosin and white light to treat skin tumors. The phototoxic effect of an administered porphyrin in man was observed in 1913. The localization of administered porphyrins in tumor tissue was recognized in the 1940s. It was not until 1972, however, that these two ideas (photodegradation of tissue and localization in tumors) came together successfully, when Diamond demonstrated that a porphyrin could preferentially degrade tumor implants in a rat (Diamond, I.; McDonagh, A. F.; Wilson, C. B.; Granelli, S. G.; Nielsen, S.; Jaenicke, R., Lancet, 1972, 1175). This result was confirmed and extended by Dougherty, T. J.; Grindey, G. B.; Fiel, R.; Weishaput, K. R.; Boyle, D. G.; J. Natl. Cancer Inst., 1975, 55, 115.

The higher concentration of porphyrins in malignant tumors is used for the treatment and detection of cancer. For detection of early stage small tumors, the porphyrin-containing tumor cells and surrounding tissues are exposed to light. The porphyrins then emit a strong fluorescence, which contrasts with the much weaker fluorescence from the normal tissue, allowing for detection. For the treatment of cancer, photodynamic therapy (PDT) consists of injecting the patient with a photoactive dye and irradiating the tumor area with a wavelength of light which activates the dye to produce toxins which kill the tumor. The porphyrin dyes become toxic to the surrounding environment by producing singlet oxygen and oxygen radicals (Dougherty, T. J.; Kaufman, J. H.; Goldfarb, A.; Weishaupt, K. R.; Boyle, D.; Mittleman, A.; Cancer Res., 1976, 38, 3628). PDT techniques depend strongly on how well the compound used preferentially concentrates within the tumor cell. Skin photosensitivity is the only known side effect of PDT with certain porphyrin type photosensitizers. Because skin retains these chemicals in enough quantities to produce surface reactions, patients must avoid exposure to sunlight.

The distribution of porphyrin drugs in the body compared with tumor cells is still under investigation. The distribution varies with cell type and porphyrin derivative. It is thought that once the photosensitizer is injected intravenously, some of the drug escapes the blood stream and moves into the interstitial fluid. The porphyrin binds to the cellular membrane and slowly diffuses into the cell cytoplasm. Each porphyrin, then, rapidly binds to hydrophobic regions inside the cell. Fluorescence microscopy of porphyrin-treated leukemia L1210 cells shows a localization around the plasma membrane and within the intracellular vesicles.

Photofrin®, a hematoporphyrin derivative (Dougherty, T. J.; Boyle, D. G.; Weishaupt, K. R., "Photodynamic Therapy—Clinical and Drug Advances, Porphyrin Photosensitization," Plenum Press, New York, 1983, p. 3) is the only photosensitizer currently being used all over the world for the treatment of a variety of solid tumors. Hematoporphyrin derivative (Hpd) is prepared by mixing hematoporphyrin with glacial acetic acid and sulfuric acid, followed by hydrolysis and precipitation under acidic conditions. This method was partially described by Lipson et al (Lipson, R. L.; Baldes, E. J.; Olsen, A. M., J. Natl. Cancer Inst., 1961, 26, 1). Hpd thus produced consists of a variety of porphyrins. When Hpd is separated into its two main fractions by gel filtration with Sephadex LH-20, the higher molecular weight portion, called Photofrin®, is a more efficient PDT agent (Dougherty, T. J.; Boyle, D. G.; Weishaupt, K. R.; Henderson, B.; Potter, W.; Bellnier, D. A.; Wityk, K. E., Adv. Exp. Biol. Med., 1983, 160, 3). The recommended human dosage of Photofrin® is 1–2 mg/kg of body weight. The main components of Photofrin® are dimers and higher oligomers linked with ether, and possibly carbon-carbon linkages (Pandey, R. K.; Siegel, M. M.; Tsao, R.; McReynolds, J. M.; Dougherty, T. J., Biomed. and Environ. Mass Spectrometry, 1990, 19, 405).

For a photosensitizer to be clinically useful, it must be non-toxic, selectively taken up and/or retained in malignant tissues, activated by penetrating light (>600 nm), and photochemically efficient. Although Photofrin® has been approved for commercialization in Canada and is expected to be approved in other countries, including the United States, it lacks rapid clearance from tissues, is a complex mixture of oligomers, and has the disadvantage that its absorbance at 630 nm is not optimized for tissue penetration. New porphyrin photosensitizers are thus needed for the improvement of photodynamic therapy for cancer treatment.

Our search for more efficient, chemically pure, less phototoxic, and better localizing porphyrins was guided by patterns recognized in the variety of new porphyrins which have recently been shown to be successful PDT agents. The important porphyrin and chlorin derivatives which have led to the development of this research have been reviewed by Pandey, R. K.; Majchrzycki, D. F.; Smith, K. M.; Dougherty, T. J., Proc. SPIE, 989, 1065, 104. The aspartyl derivatives of chlorin $e_6$, monoaspartyl chlorin $e_6$ and diaspartyl chlorin $e_6$, were found to be effective photosensitizers in vitro (Roberts, W. G.; Shaiu, F. Y.; Nelson, J. S.; Smith, K. M., Roberts, M. W., J. Natl. Cancer Inst., 1988, 80, 330). With these compounds, the aspartyl group was noted to be responsible for the efficiency of tissue clearance. In pheophorbide, pyropheophorbide and chlorin $e_6$ series, certain alkyl ether derivatives including 2-(1-hexoloxyethyl)2-des vinyl derivatives were found to be excellent photosensitizers compared with parent compounds, methyl pheophorbide-a, pyropheophorbide- and chlorine$_6$. (Pandey, R. K.; Bellnier, D. A.; Smith, K. M.; Dougherty, T. J., Photochem. Photobiol., 1991, 53, 65). This was attributed to the increased hydrophobicity of the hexyl group and is consistent with studies done by Evensen on porphyrins with varying polarities (Evenson, J. F.; Sommer, S.; Riminfton, C.; Moan, J., Br. J. Cancer, 1987, 55, 483).

Chang, C. K., Sotiroiu, C.; Wu, W., J. Chem. Soc., Chem. Commun., 1986, 1213, have previously shown that chlorins, on reacting with osmium tetroxide can be converted to vic dihydroxy bacteriochlorin system. We extended this methodology in the pheophorbide-a and chlorin $e_6$ series, and prepared a series of vic -dihydroxy and keto-bacteriochlorins (Pandey, R. K.; Shiau, F. Y.; Sumlin, A. B.; Dougherty, T. J.; Smith, K. M., Bioorg. & Med. Chem. Lett., 1992, 2, 491). It has also been reported that the regiospecificity of pyrrole subunits in osmium tetroxide oxidation is affected significantly by the presence of electron withdrawing substituents in the macrocycle(5a). These stable bacteriochlorins, prepared from mesochlorin $e_6$ trimethylester and pyropheophorbide-a methylester, have strong absorption in the red region (730 to 750 nm), but, did not show any significant in vivo photosensitizing activity (Kessel, D.; Smith, K. M.; Pandey, R. K.; Shaiu, F. Y.; Henderson, B., Photochem. Photobiol., 1993, 58, 200).

A few years ago, Hoober, J. K.; Sery, T. W.; Yamamoto, Y., Photochem. Photobiol., 1988, 48, 579 have shown that purpurin-18 2, which has strong absorption at 700 nm might be useful photosensitizer for photodynamic therapy (PDT).

Among long wavelength absorbing photosensitizers, bacteriochlorins have been proposed as potential useful candidates for use in photodynamic therapy (PDT) where strong absorptions in the visible spectrum can be used to photoactivate dyes previously located in targeted (neoplastic) tissues (Pandey, R. K.; Shiau, F. Y.; Isaac, M.; Ramaprasad, S.; Dougherty, T. J.; Smith, K. B., Tetrahedron Lett., 1992, 33, 7815). Some naturally occurring bacteriochlorins, have previously been reported as effective photosensitizers both in vitro and as in vivo (Beems, E. M.; Dubbelman, T. M. A. R.; Lugtenburg, J.; Best, J. A. B.; Smeets, M. F. M. A.; Boehgeim, J. P. J., Photochem. Photobiol., 1987, 639). However, most of the naturally occurring bacteriochlorins (760–780 nm) are extremely sensitive to oxygen, which results in rapid oxidation to the chlorin state (640 nm); thus the spectroscopic properties of the bacteriochlorins are lost. Further, if a laser is used to excite the bacteriochlorin in vivo, oxidation may result in the formation of a new chromophore absorbing outside the laser window, thus reducing the photodynamic efficiency.

BRIEF DESCRIPTION OF THE INVENTION

Figure 1:
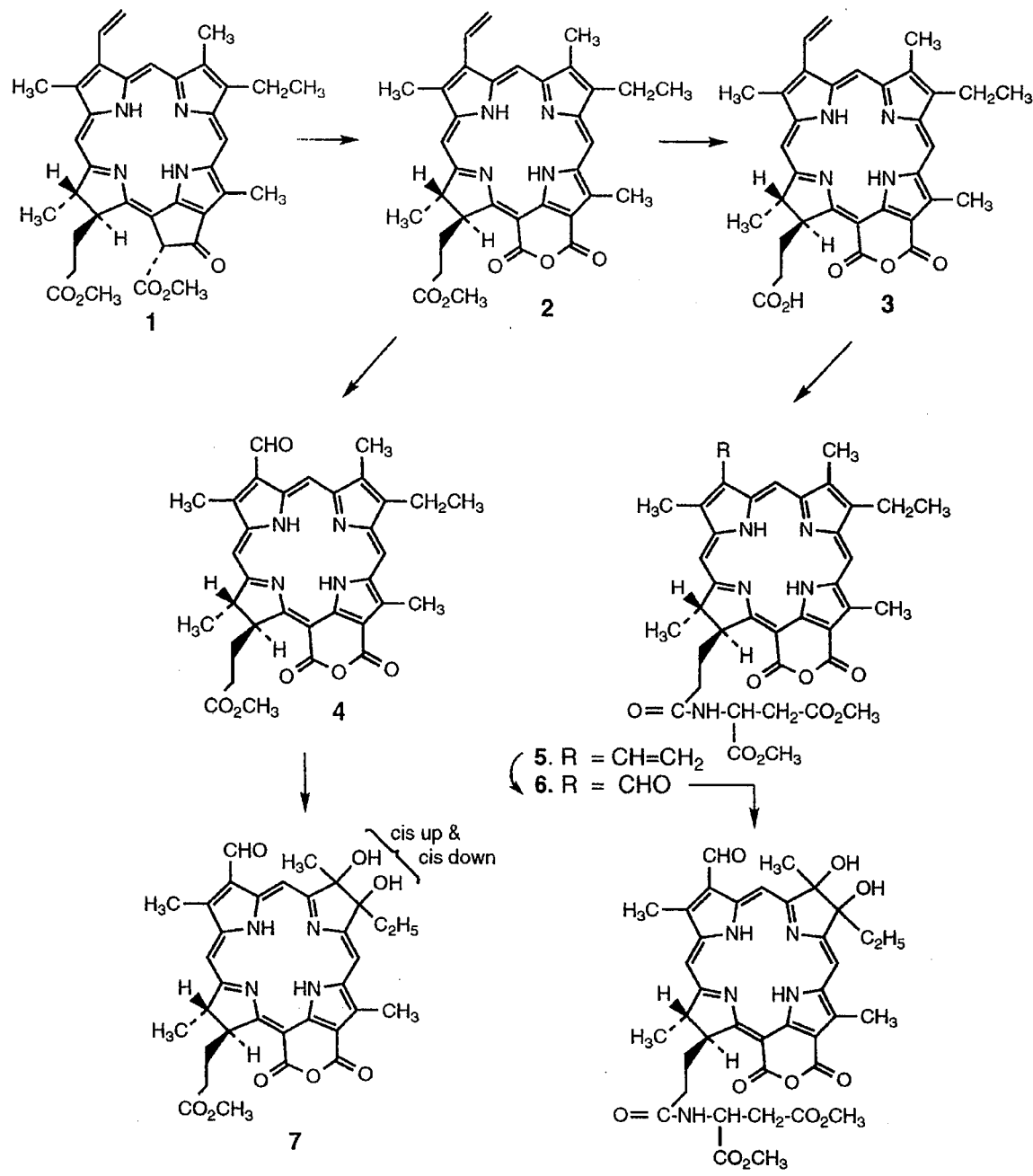
FIG. 1 is a schematic equation showing the synthetic route to compounds 7 and 8.
Figure 2:
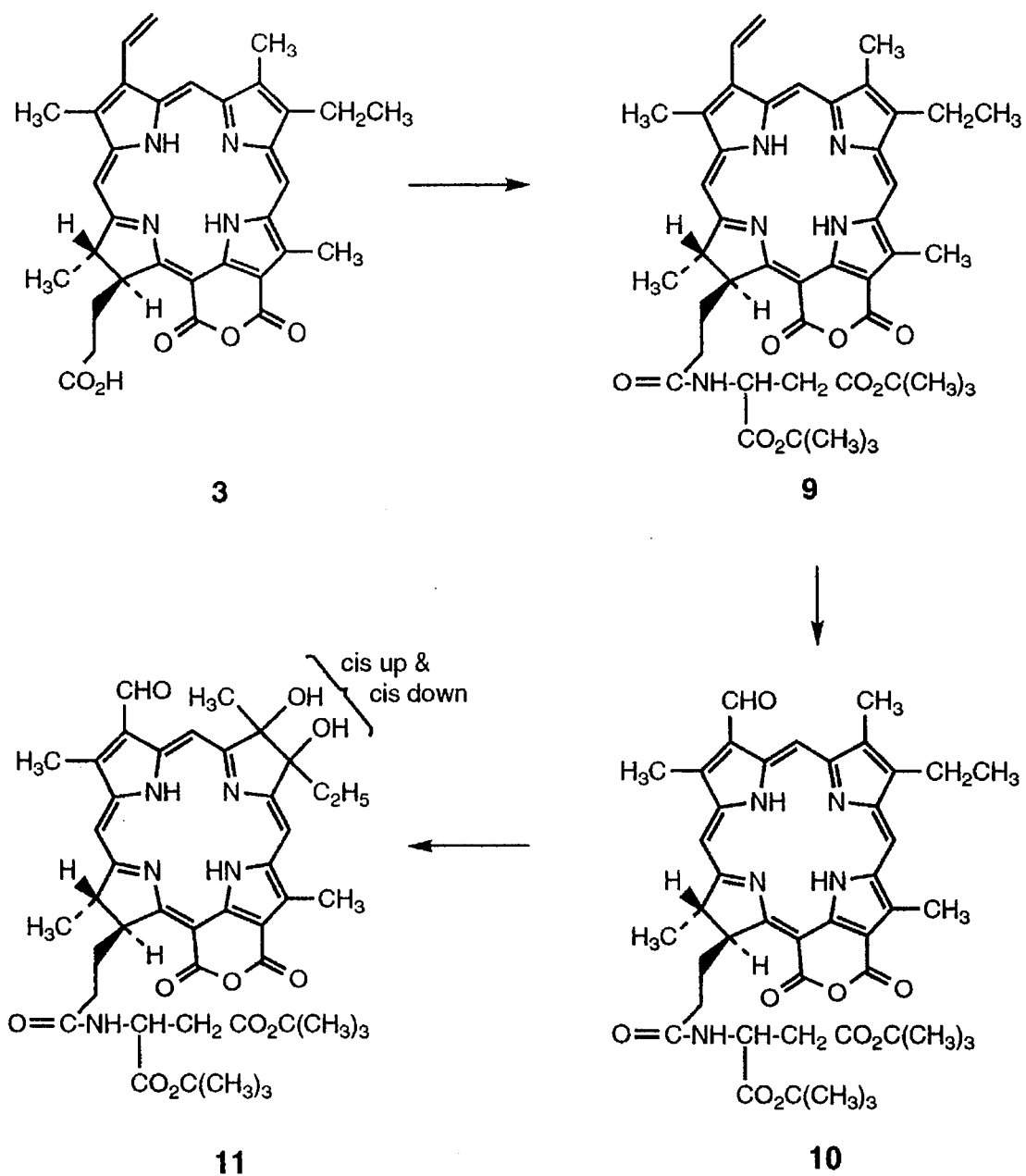
FIG. 2 is a schematic equation showing the synthetic route to compound 11.
Figure 3:
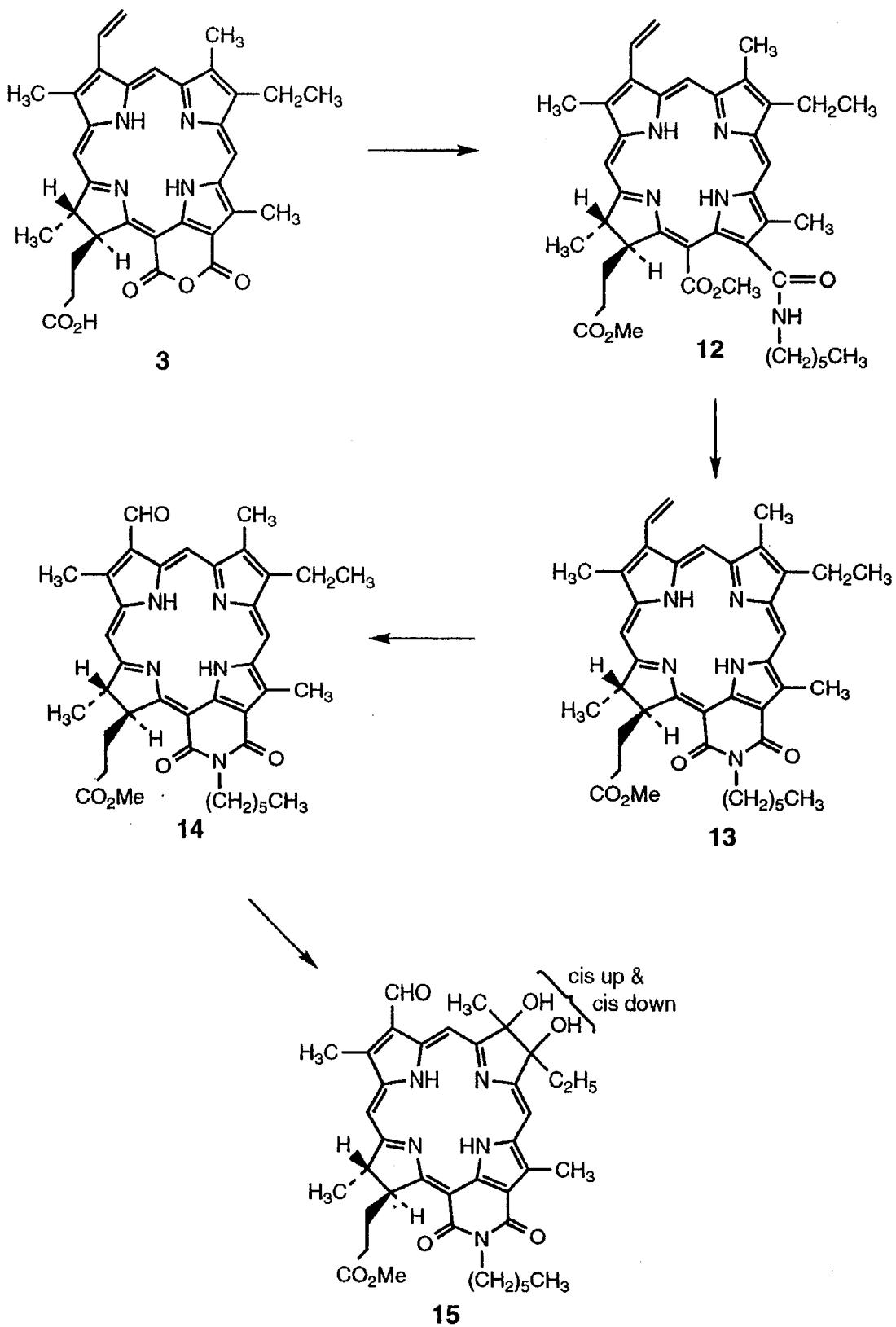
FIG. 3 is a schematic equation showing the synthetic route to compound 15.
Figure 4:
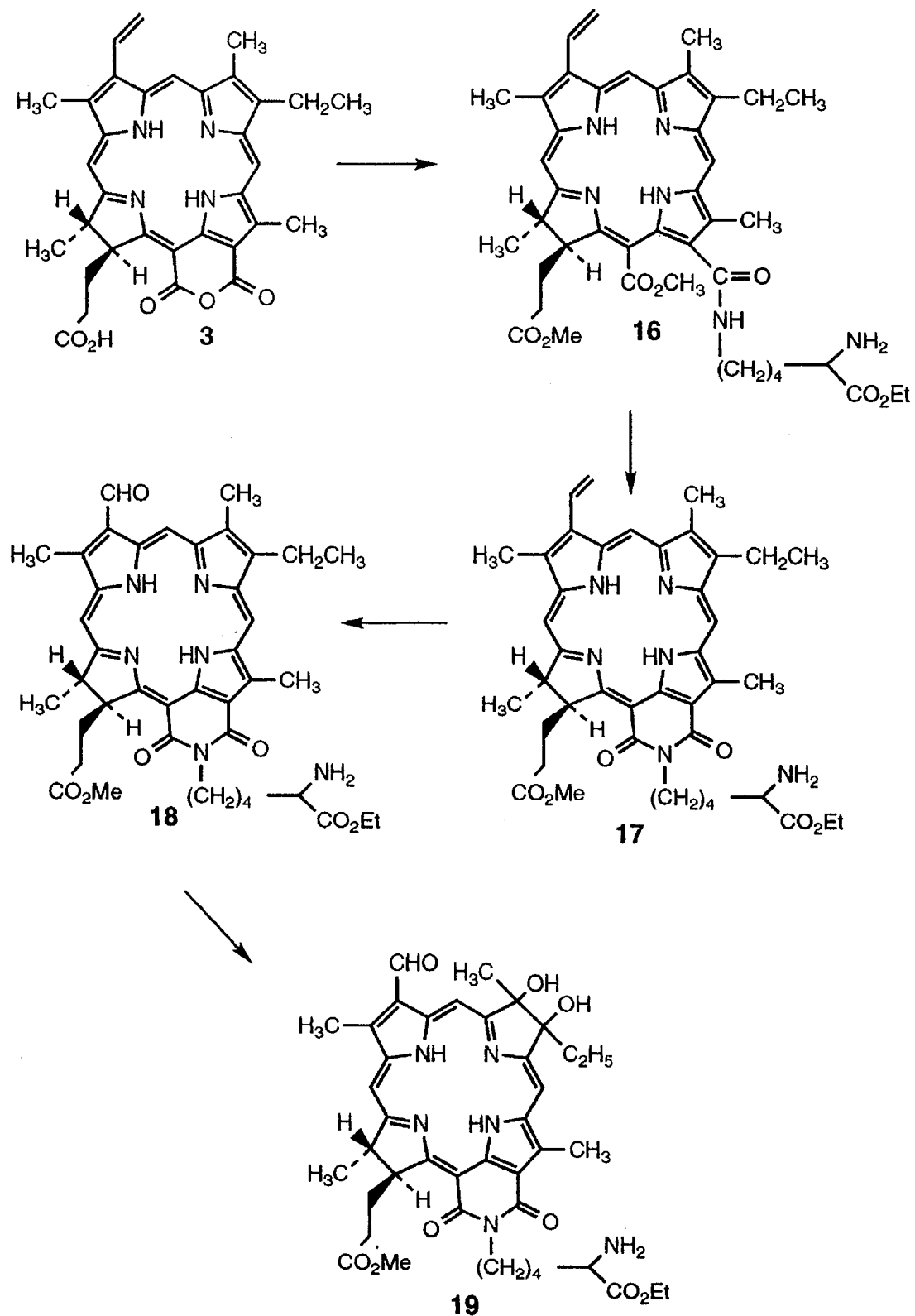
FIG. 4 is a schematic equation showing the synthetic route to compound 19.

In accordance with the present invention, there are provided new benzoporphyrin derivatives having utility as fluorescent and photosensitizing compounds. Such compounds may be excited by microwaves, ultrasound, and visible or infrared radiation.

All of such novel compounds described herein may be used in traditional areas where compounds having such properties have utility. The compounds, may, for example, be incorporated into a substance such as a plastic product, excited with ultrasound, microwaves or visible light followed by using known methods for detecting emitted radiation to image the product for the purpose of detecting voids or other flaws in the product.

Certain of such compounds have special utility as photosensitizers in the area of photodynamic therapy for the detection and treatment of tumors.

Chlorin-$e_6$ esters were found to be less effective than methyl pheophorbide-a, and pyropheophorbide-a analogs, indicating that either the E-ring is an important factor in photoactivity or due to its increase in hydrophilicity, it does not retain in the tumor cells for longer time than the n-hexyl or n-heptyl ether derivatives of pyropheophorbide-a. Among newer photosensitizers, some benzoporphyrin derivatives (BPD) as a mixture of isomers, obtained by Diels Alder reaction on protoporphyrin IX dimethyl ester, has also been reported as efficient photosensitizer. We further expanded the chemistry of BPD, and prepared a series of alkyl ether derivatives. These derivatives were found to be more active than corresponding vinyl analogues (the parent molecule).

In accordance with the invention, to make PDT more applicable, there is a need of long wavelength absorbing photosensitizers such as stable bacteriochlorins which have the ability to localize in high concentration at the tumor site.

In accordance with the invention, a compound is therefore provided which comprises a chemical of the formula:

[Structural formula of benzoporphyrin derivative with substituents $R_1$, $R_2$, $R_3$, $R_4$, $R_5$, Z, and methyl groups]

where Z is =O or =$NR_6$, where $R_6$ is lower alkyl of from 1 to 8 carbon atoms or $$-(CH_2)_4-\underset{NH_2}{CH}-CO_2Et;$$

$R_1$ is $$-\underset{O}{\overset{\parallel}{C}}-R_7,$$

where $R_7$ is $$-N\underset{H}{R_8}$$

or —$OR_8$, where $R_8$ is hydrogen or lower alkyl of 1 to 8 carbon atoms, or $R_7$ is an amino acid residue connected at a nitrogen atom of such residue; $R_2$ is lower alkyl or lower alkylene of from 2 to 4 carbon atoms or a formal or carbonyl containing group of from 1 to 4 carbon atoms; $R_3$ and $R_4$ are —H or —$OR_8$ or are joined together so that each represents one-half of a chemical bond and $R_4$ may be taken together with $R_5$ to form =O; and $R_5$ is ethyl or is taken together with $R_4$ to form =O; provided that when Z is —O— the sum of the number of carbon atoms in $R_1$ through $R_5$ is from 12 to 20 and when Z is =$NR_6$, the sum of the number of carbon atoms in $R_1$ through $R_6$ is 8 to 20.

DETAILED DESCRIPTION OF THE INVENTION

In order to prepare long wavelength absorbing photosensitizers, we modified purpurin-18, and two new bacteriochlorin systems, e.g., shown as structural formula 2, {in which a six membered anhydride ring is fused to the macrocycle}and e.g., 9, {in which the anhydride ring is replaced by an imide ring system}. Purpurin-18 methylester 2 was obtained from methyl pheophorbide-a 1 using a synthesis procedure known for other purposes (Kenner, G. W.; McCombie, S. W.; Smith, K. M., *J. Chem. Soc., Perkin Trans. I*, 1973, 2517). The anhydride ring in 2 was replaced with imide ring system 17 by first reacting purpurin-18 3 with lysine at room temperature. The intermediate, 6, which has strong absorption at 660 nm was isolated in 80% yield. Various reaction conditions (Lee, S. J. H.; Jagerovic, N.; Smith, K. M., *J. Chem. Soc., Perkin Trans I*, 1993, 2369) were used to convert the open chain amide to its cyclic derivative analogue 17, and the best results were obtained when the intermediate amide as stirred with montmorillonite K10 (Aldrich) in methylene chloride. The reaction was monitored by spectrophotometry. Like purpurin-18 methylester 2, the cyclic imide 18 also had strong absorption at 702 nm. The other imide derivative 13, was prepared by following the similar approach, except purpurin-18 methylester 2 was reacted with 1-hexyl amine instead of L-lysine. For the preparation of formyl analogues 4, 6, 10, 14 and 18, the corresponding vinyl derivatives 2, 5, 9, 13 and 17 were reacted with osmium tetroxide/sodium periodate as has been done for other compounds (Pandey, R. K.; Shiau, F. Y.; Sumlin, A. B.; Dougherty, T. J.; Sumlin, K. M., *Bioorg. Med. Chem. Lett.*, in press) and were isolated in excellent yield.

Figure 9:
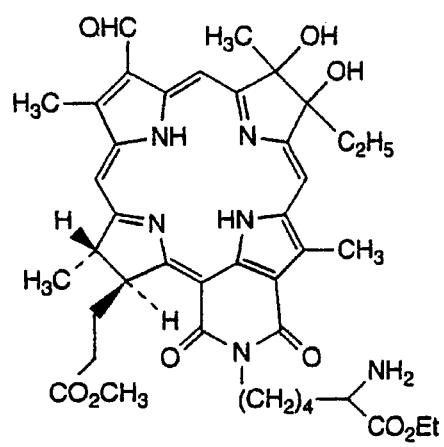
FIG. 9 is a curve showing the light absorbance of compound 11.
Figure 9:
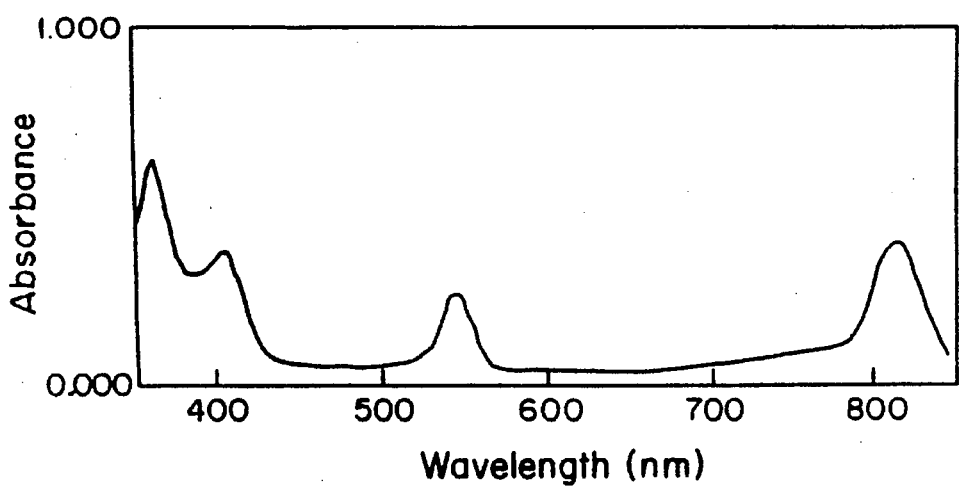

It has been shown that among certain photosensitizers, by converting the methyl esters to corresponding aspartyl acid derivatives make significant increase in photosensitizing efficacy. In order to examine the effect of such substituents in our newly synthesized bacteriochlorin systems, purpurin-18 methylester 2 was converted to corresponding carboxylic acid 3 by acid hydrolysis. It was then reacted with DCC, aspartic acid dimethyl ester along with a catalytic amount of dimethyl amino pyridine (DMAP), using freshly distilled tetrahydrofuran as a solvent. The desired aspartic derivative was isolated in 75% yield. The other derivatives were prepared by following the same approach and in almost the same yield. The formyl derivative, e.g., 10 was prepared by following the methodology as discussed for the methylester analogue 4. For the synthesis of vicdihydroxy bacteriochlorin 7, 8, 11, 15 and 19 the respective vinyl analogues were individually reacted with osmium trioxide/pyridine, and then with hydrogen sulfide gas. The crude residue was purified by either silica column chromatography or by preparative plates, and the desired products were isolated in 60 to 70% yield. As shown in FIGS. 9 (for 11) and 8 (for 19) and in Tables A and B respectively, the formyl bacteriopurins 7, 8 and 10 and related imide derivative 15 and 19 have strong absorptions at 815 nm.

TABLE A

| | Compound 11 | | | |
|---|---|---|---|---|
| | PEAK | | VALLEY | |
| NO. | nm | ABS | nm | ABS |
| 1 | 813.0 | 0.337 | 623.0 | 0.046 |
| 2 | 602.0 | 0.052 | 600.0 | 0.046 |
| 3 | 546.0 | 0.231 | 490.0 | 0.054 |
| 4 | 404.0 | 0.328 | 381.0 | 0.233 |
| 5 | 360.0 | 0.518 | | |

TABLE B

| | Compound 19 | | | |
|---|---|---|---|---|
| | PEAK | | VALLEY | |
| NO. | nm | ABS | nm | ABS |
| 1 | 816.0 | 0.386 | 806.0 | 0.040 |
| 2 | 602.0 | 0.045 | 600.0 | 0.039 |
| 3 | 546.0 | 0.242 | 488.0 | 0.052 |
| 4 | 406.0 | 0.360 | 383.0 | 0.296 |
| 5 | 361.0 | 0.605 | | |

Figure 5:
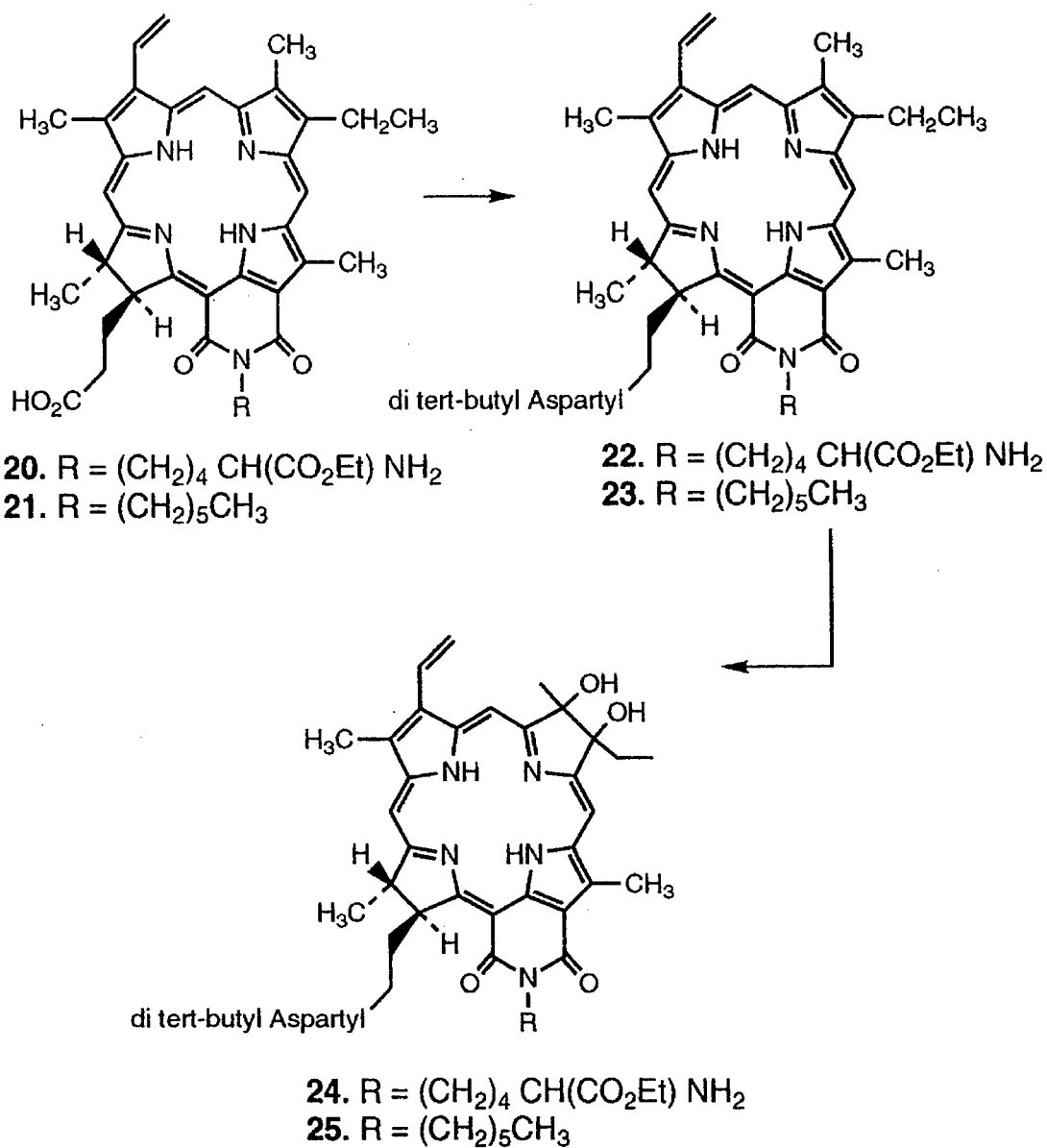
FIG. 5 is a schematic equation showing the synthetic route to compounds 24 and 25.

Some of the bacteriochlorins 7, 8, 10 and 19 were evaluated for in vivo photosensitizing efficacy. The preliminary results are summarized in Table 1. From these results it can be seen that formyl bacteriopurpurin-18 methylester 7 and aspartic acid di methyl ester 8 were found to be biologically inactive at a dose of 5.0 mg/kg, when treated 3h post i.v. injection of the drug. However, under similar treatment conditions, its aspartic acid di-tert butyl ester derivative 10 showed promising activity (80% tumor control, day 30). Bacteriochlorin 19, which still had propionic ester side chain at position 7, but wherein the anhydride ring has been replaced by imide ring system (R=L-lysine) showed much better activity (100% tumor control, day 7, tumor control, day 30) than formyl bacteriopurpurin-18 7 and 8 (no tumor cure at all). Comparing the biological results of bacteriopurpurin 7 and 8 with be, it is evident that aspartic acid substituents containing tert- butylester groups make significant difference in biological activity. Thus, we believe that the anti-tumor activity of bacteriochlorin 19 might be further increased by replacing the methylester with aspartic acid di tert-butylester side chain e.g., 24 and 25 (FIG. 5). The low activity of photosensitizers 7 and 8 might be due to the hydrolysis of the methyl esters to corresponding carboxylic acids by the enzyme esterases, which of course will make these photosensitizers extremely hydrophilic, and thus will diminish their ability to be retained in the tumor cells for longer time (Pandey, R. K. and Dougherty, T. J., *Photochem. Photobiol.*, 1988, 47, 769). Further biological studies with these photosensitizers at different doses and time intervals are in progress.

Figure 7A:
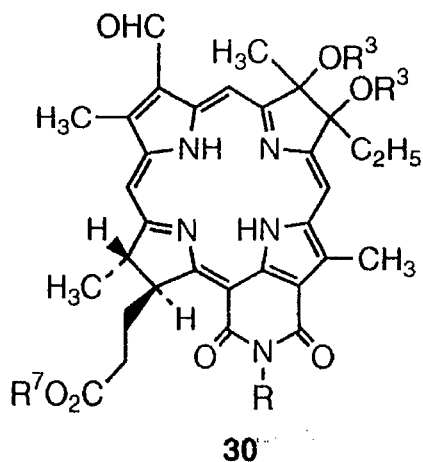
FIGS. 7A through 7C show the structures of compounds 30, 31 and 32, respectively.
Figure 7B:
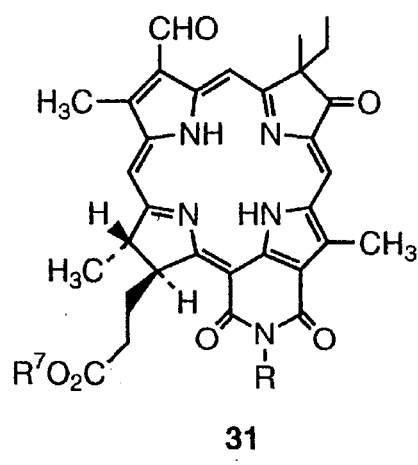
Figure 7C:
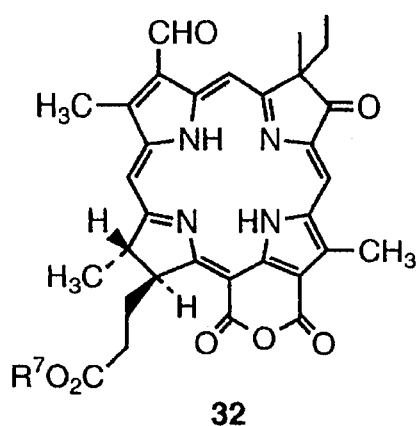
Figure 8:
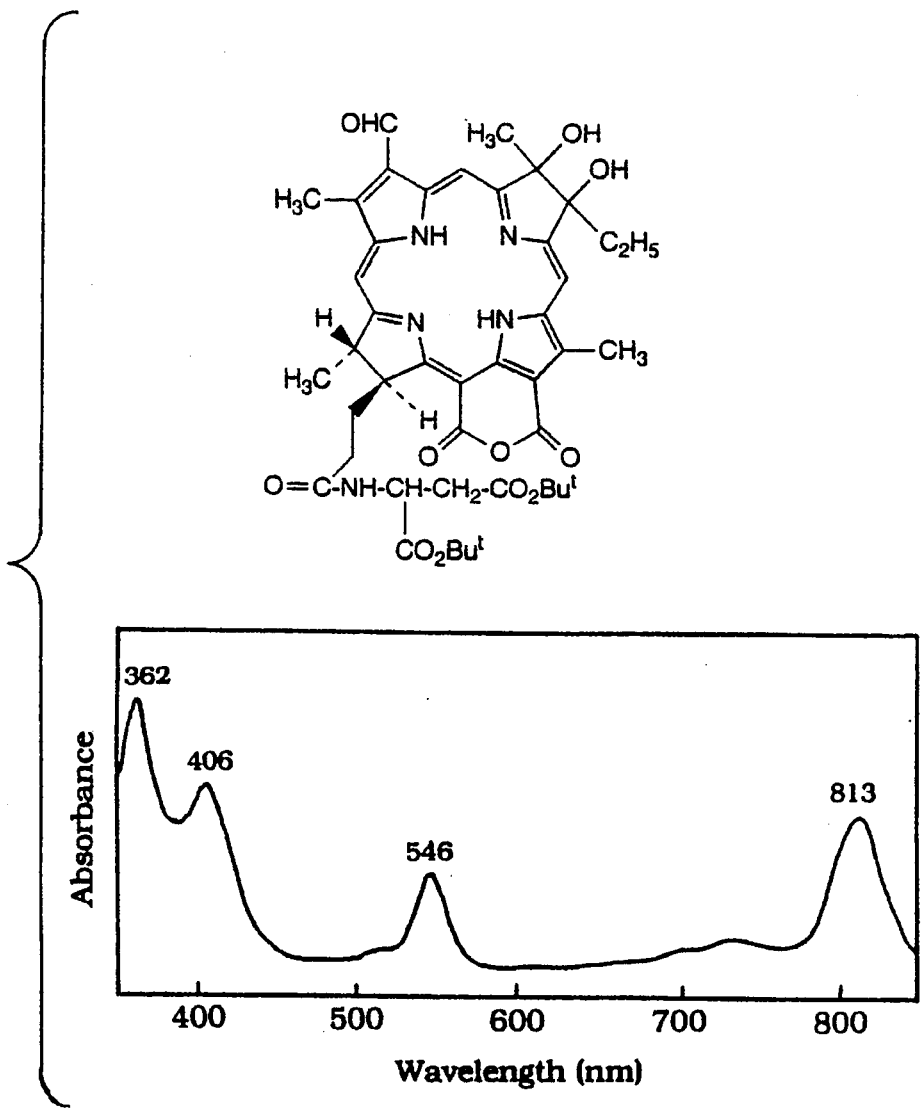
FIG. 8 is a curve showing the light absorbance of compound 19.

From these and previously reported results (Bellnier, D. A.; Henderson, B. W.; Pandey, R. K.; Potter, W. R.; Dougherty, T. J., *J. Photochem. Photobiol.*, 1993, 20, 55) it seems that hydrophilicity/hydrophobicity makes a remarkable difference in localizing a photosensitizer in tumors, and, it should be considered as one of the most important requirements in designing an effective photosensitizer. In order to make the newly synthesized bacteriochlorins more hydrophobic, attempts are currently being made to prepare the alkyl ether derivatives with variable carbon units (1 to 6), and respective keto bacteriopurpurin with anhydride or imide linkages, e.g., 30 and 31 respectively (FIGS. 7A–7C). These new photosensitizers may be evaluated for their in vivo photosensitizing activity.

Experimental:

Melting points (MP) are uncorrected and were measured on a Fisher Johns melting point apparatus. Electronic absorption spectra were measured on a Hewlett Packard 8450A spectrophotometer or Perkin Elemer 3000 spectrophotometer using solutions in dichloromethane unless otherwise stated. Mass spectra were measured at the Department of Biophysics, Roswell Park Cancer Institute, Buffalo, N.Y. Proton NMR spectra were obtained at 300 MHz on a General Electric QE-300 spectrometer or 270 Joel at the State University of New York, Buffalo, N.Y. Samples were dissolved in $CDCl_3$ and chemical shifts are reported relative to $CHCl_{13}$ at 7,258 ppm unless stated otherwise.

Analytical thin-layer chromatography was used to monitor reactions and to check purity of the desired compounds on cut strips (ca. 2 cm×6 cm) of Merck or Whatman silica gel 60 F254 precoated (0.25 mm thickness) plastic backed sheets. Preparative TLC was performed on a freshly prepared glass plated (20 cm×20 cm) coated with a ca 2 mm thick Merck silica gel CF254. Plates were activated prior to use by heating to 110° C for at least 8 hours. For column chromatography two types of packing was used: (i) Alumina was deactivated with 6% water (Brockman Grade III) before use; and (ii) Silica gel 60 (70–230 mesh) was used for normal gravity chromatography and silica gel 60 (230–400 mesh) was used for flash chromatography. Pressure for the later was supplied by house compressed air.

Before injecting the drug to animals the purity of the material was checked by HPLC, and it was performed using a Spectra-Physics system connected to SP8 700 solvent delivery system, Kratos 757 absorption detector with a fixed wavelength at 405 nm. Two solvent compositions were used in the HPLC analysis: (i) solvent A was prepared by dissolving anhydrous dibasic sodium phosphate (1.0 g) in 400 ml water. To this was added HPLC grade methanol (600 ml). The pH of the solution was adjusted to 7.5 with phosphoric acid; and (ii) solvent B was prepared by dissolving anhydrous dibasic sodium phosphate (0.3 g) in 100 ml water, and to this was added methanol (900 ml) and the pH was adjusted to 7.5 with phosphoric acid. For most of the photosensitizers (as methyl- or aspartylacid ditert-butylester derivatives) solvent B was used as isocratic mode (column, reverse phase C-8, flow rate 1.5 ml/min). For the intermediates as carboxylic acids, solvent A and solvent B were used as gradient mode (0.1–0 min A, 10–40 min A-B, 40–50 min B, 50–60 min back to A).

Tetrahydrofuran (THF) was distilled over sodium before use. All other solvents were used as commercially available (ACS grade). The phrase dried and filtered and evaporated means drying over sodium sulfate, filtering through glass wool, and then evaporating off the volatile solvent using a Buchi rotary evaporator under house vacuum or high vacuum achieved with an oil pump.

Purpurin-18 methyl ester 2: Methyl pheophorbide-a 1 (700 mg) was dissolved in warm pyridine (10 ml) and the solution was diluted with ether (500 ml). The solution was stirred with a stream of air passing through it, and a solution of KOH (8.0 g) in propanol (20 ml) was added. The bright green mixture was stirred and aerated for 30 min and then extracted with water until the ethereal layer was no longer green. The ethereal solution layer was discarded, the aqueous extracts were combined, adjusted to pH 4 with conc sulfuric acid (8 ml) in water (40 ml), and extracted with dichloromethane until the aqueous layer was no longer green-brown. The combined dichloromethane extract containing unstable chlorin was subjected to repeated evaporation and redissolution in THF (freshly distilled) until no further increase in visible absorption at 700 nm was observed. The product was esterified with ethereal diazomethane and then washed with water, dried and evaporated to dryness. The product was purified by silica column, eluting with 2% methanol in dichloromethane. The appropriate eluates were combined, and the residue obtained evaporating the solvents was crystallized from dichloromethane/methanol to give the title compound in 50% yield (290 mg). m.p. >260° C. (decomp.) (lit., 260–280° C.). max 698 ( ), 642 ( ), 592 ( ), 546 ( ), 508 ( ), 478 ( ) and 410 ( ). NMR ppm 9.55, 9.35, 8.57 (meso H), 7.88 (dd, 11.7, 2-a H), 6.29 (d, 2b-H), 6.18 (d, 2b'H), 5.17 (d, 7-H), 4.38 (q, 8-H), 3.76 (s, 3H), 2.73 (m, 7b-H), 2.47 (m, 7b'H), 2.43 (m, 7a-H), 1.99 (m, 7a'H), 1.74 (d, 8 Me), 1.65 (t, 4b-Me) and 2.01 and −0.09 (each br s, NH); (HRMS 78.2509. $C_{34}H_{34}N_4O_5$ requires 578.2529.

Purpurin-18 carboxylic acid 3: Purpurin-18 methyl ester (250 mg) was dissolved in dry THF (40 ml), aqueous HCl (4N) [100 ml]was added. The reaction mixture was stirred under nitrogen, and the reaction was monitored by analytical TLC. The reaction mixture was extracted with dichloromethane, washed with water till the pH of the aqueous phase in neutral. The organic phase was dried over anhydrous sodium sulfate, and the solvent was evaporated. The residue was crystallized from $CH_2Cl_2$/hexane as fine powder. Yield 80%. m.p.>300° C. The NMR spectrum was same as discussed for the methyl ester except the resonances for the —OMe was missing.

Purpurin-18 asparticacid di-tert butylester 9: Purpurin-18 carboxylic acid 3 (200 mg) was dissolved in dry THF (100 ml). Dicyclohexylcarbodiimide (DCC, 250 mg), aspartic acid ditert butyl ester hydrochloride ( 200 mg), and dimethylaminopyridine (DMAP, 20 mg) was added to the reaction mixture. It was then stirred at room temperature for over night under nitrogen atmosphere. The reaction was monitored by analytical TLC. The reaction mixture was diluted with dichloromethane (200 ml), washed with water. The organic layer was separated, dried and evaporated. The residue was purified by preparative plates, using 5% methanol/dichloromethane. The major band was collected, washed with 5% methanol/dichloromethane till the silica is free from the title compound. Evaporation of the solvent and crystallization from dichloromethane/hexane gave the desired aspartyl derivative. Yield 160 mg. $^1$H NMR (ppm): 9.30, 9.18, 8.54 (each H. 1H, meso H), 8.18 (dd, 1H, 2a-CH), 6.61 (d, 1H, Asp —NH), 6.27 (d, 1H, 2b-CH), 6.16 (d, 1H, 2b-CH cis to 2a-CH), 5.17 (d, 1H, 7-H), 4.67 (X Of ABX, 1H, Asp-CH), 4.31 (q, 1H, 8-H), 4.05 (q, 2H, 4a-CH2), 3.59, 3.31, 3.03 (each s, 3H, $CH_3$), 3.58 (m, $CH_2CH_2CO$), 2.84, 2.73 and 2.48 (7b-CH, ABX 2H, Asp —$CH_2$), 1.72 (d, 3H, 8 $CH_3$), 1.58 (t, 3H, 4-$CH_2CH_3$). 1.39, 1.37 (each s, 9H, O-tert-butyl), 0.067 and −0.194 (each br s, 1H, NH).

Purpurin-18 aspartic acid dimethylester 5: Purpurin-18 carboxylic acid (200 mg) was dissolved in dry THF (100 ml) and reacted with aspartic acid dimethyl ester (200 mg), DCC (250 mg), DMAP (20 mg) by following the method as discussed for the foregoing aspartic acid di tert butyl ester derivative, and the title compound was isolated in 80% yield.

2-Formyl-purpurin-18 methylester 4: Purpurin-18 methyl ester (540 mg) was dissolved in THF (100 ml). 1,4-Dioxane (20 ml), water (20 ml), carbontetrachloride (10 ml), osmium tetroxide (70 mg) and sodium periodate (600 mg) were added to the reaction mixture and the reaction mixture was stirred at room temperature and the reaction was monitored by analytical TLC and by spectrophotometry (disappearance of a peak at 700 nm, and appearance of a new peak at 734 nm). It was then diluted with dichloromethane (200 ml), washed several times (3×100 ml) with 2% aqueous acetic acid, and again with water. The organic phase was evaporated after drying over anhydrous sodium sulfate. The residue was purified by silica column eluting with 5% methanol/ dichloromethane. The major band was collected, solvents were evaporated and the product was crystallized from $CH_2Cl_2$/hexane. Yield 80%. (mg). m.p. $^1$H NMR (ppm), 11.32 (s, H, CHO), 10.10, 9.52, 8.75 (each s, 1H, 3X meso H), 5.40 (d, 1H, 7-H), 4.40 (q, 2H, 4a-$CH_2$), 4.02 (s, 3H, $OCH_3$), 3.82 (t, 2H, $CH_2CH_2CO$), 3.80, 3.65, 3.56 (each s, 3H, 3 $XCH_3$), 2.5–2.70 (m, H, 7b-$CH_2$), 1.78 (d, 3H, 8-$CH_3$), 1.62 (t, 3H, 4-$CH_2CH_3$), −0.30 (br s, 2H, 2XNH).

2-Formyl-purpurin-18 asparticacid di tert-butylester 10: Purpurin-18 aspartylacid ditert butylester 4 (150 mg) was reacted with osmium tetroxide/sodium periodate by following the procedure as discussed for the formyl derivative, and the respective formyl analogue was isolated in 75% yield. m.p. max; $^1$H NMR (ppm): 11.52 (s, 1H, CHO), 10.70, 9.82, 8.92 (each s, 1H, 3X meso H), 6.70 (d, 1H, Asp NH), % 0.42 (d, 1H, 7-H), 4.62 (X of ABX, 1H, Asp CH), 4.20 (q, 2H, 4a-$CH_2$), 4.00, 3.82, 3.36 (each s, 3H, 3X$CH_3$), 3.62 (m, 2H, $CH_2CH_2CO$), 3.00, 2.84, 2.50 (7b-$CH_2$ ABX, 2H, Asp $CH_2$), 1.62 1nd 1.60 (each s, 9H, —O-tert-butyl), 0.00 (Brs, 2H, 2XNH).

2-Formyl-purpurin-18 asparticacid dimethyl ester 6: Purpurin-18 aspartic acid dimethylester (200 mg) was converted to corresponding formyl derivative as discussed for other formyl derivatives. The desired product was isolated in 70% yield. Chlorin-$p_6$ 6-lysylethoxyamide, 7-methyl ester 16, and Purpurin-N-lyselethoxi imide-7-methyl ester 17: To lysine ethyl ether, prepared by naturalization of lysine ethyl ester dihydrochloride (5 mg, 20 mmol) with aqueous KOH, purpurin-18 methyl ester (350 mg, 0.606) in chloroform (100 ml) was added. This mixture was stirred at room temperature under nitrogen overnight. The reaction was monitored by spectrophotometry (appearance of a peak at 665 nm, and disappearance of the peak of the starting material at 700 nm) and was worked up by following the standard methodology. The intermediate thus obtained was immediately dissolved in dichloromethane (100 ml) and montomorillonite K 10 (1 g) was added. The reaction mixture was stirred at room temperature under nitrogen, and was monitored by uv-vis spectroscopy (appearance of a new peak at 700 nm, and disappearance of the starting material peak at 665 nm). The reaction mixture was then filtered. Solvent was evaporated and the residue was purified by silica column, eluting with 2% methanol/dichloromethane. The title imide derivative was isolated in 60% yield starting from purpurin-18 methyl ester. m.p 132°–33° C. Analysis: Found: c, 68.7; H, 6.7; N; 11.3 $C_{42}H_{50}N_6O_6$ requires: C, 68.63; N, 6.86; N, 11.44%. max/nm 706 ( ), 664 ( ), 548 ( ), 510 ( ), 484 ( ), 418 ( ). ppm 9.56, 9.33, 8.59 (each s, meso H), 7.89 (dd, 2a-H), 6.29 (d, 2b-H), 6.16 (d, 2b'H) 5.40 (d 7-H) 4.49 (m 6-lysine $CH_2$), 4.36 (q, 8-H), 4.22 (q, 6-lysine —$CO_2CH_2$), 3.81 (s, 3H), 2.80–2.30 (m, 7-$CH_2CH_2$), 2.46 (m,-lysine-H), 1.79 (d, 8-Me), 1.66 (t, 4b-Me), 1.31 (t, 6-lysine-$CO_2CH_2CH_3$), −0.08 (br s, NH) and −0.17 (br s, NH) {Found m/z (HRMS) 734.3784. $C_{42}H_{50}N_6O_6$ requires 734.3792}.

Chlorin-$p_6$ 6-N-hexylamide-7-methyl ester 12: A solution of purpurin-18 methyl ester (500 mg) in dichloromethane 950 ml) was cooled to 0° C. and n-hexylamine (1.0 ml) was added to it. The reaction mixture was stirred at room temperature overnight under inert atmosphere, whereupon spectrophotometry and TLC showed the absence of starting material. The reaction mixture was then diluted with dichloromethane, washed with water. The dichloromethane layer was dried over anhydrous sodium sulfate, and evaporated to dryness, eventually with the oil pump to remove traces of hexylamine. The product was purified by preparative plates, eluting with 5% methanol/dichloromethane. After evaporation of the solvents, the residue was crystallized from $CH_2Cl_2$/hexane in 90% yield. $^1$H NMR: Due to aggregation, the NMR spectrum of the title compound was complex, and it was difficult to assign the resonances for all the protons.

Purpurin-N-hexylamide-7-methyl ester 13: The foregoing hexylamide derivative (mg) was dissolved in dichloromethane (ml), and montomorillonitr K 10 (mg) was added to it. The reaction mixture was stirred at room temperature under nitrogen atmosphere and the reaction was monitored by spectrophotometry. K-10 clay was washed several times with 5% methanol/dichloromethane. The filtrate so obtained was evaporated, and the imide derivative was crystallized from $CH_2Cl_2$/hexane as fluffy solid. $^1$H NMR (ppm): 9.45, 9.30 and 8.88 (each s, 1H, 3X meso H), 7.82 (dd, 1H, 2a-CH), 6.20 (dd, 2H, 2b-$CH_2$), 5.12 (d, 1H, 7-H), 4.40 (q, 2H, 4-$CH_2$ $CH_3$), 3.70 (s, 3H, —$OCH_3$), 3.52 (t, 2H, $CH_2CH_2CO$), 3.62, 3.35, 3.12 (each s, 3H, 3X$CH_3$), 2.40–2.70 (m, 7b-$CH_2$), 1.70 (d, 3H, 8-$CH_3$), 1.52 (t, 3H $CH_2CH_3$), 0.10 and −0.20 (each br s, 1H, 2XNH).

2-Formyl-purpurin-N-hexylimide-7-methyl ester 14: The foregoing imide derivative X (100 mg) was converted to corresponding formyl analogue by reacting with osmium tetroxide/sodium periodate as discussed for the preparation of other formyl derivatives. $^1$H NMR (ppm): 11.34 (s, 1H, CliO), 10.12, 9.60, 8.75 (each s, 1H, 3X meso H), 5.22 (d, 1H, 7-H), 4.40 (q, 2H, 4-$CH_2CH_3$), 3.75, 3.65, 3.60 and 3.15 (each s, 3H, 1X $OCH_3$, and 3X$CH_3$), 3.60 (t, 2H, $CH_2CH_2CO$), 2.40–2.70 (m, 2H, 7b-$CH_2$), 1.74 (d, 3H, 8-$CH_3$), 1.62 (t, 3H<4-$CH_2CH_3$), 0.80 to 1.60 (N-Hexyl), −0.30 (brs, 2H, 2XNH).

2-Formyl-vic-dihydroxy bacteriopurpurin-N-hexylimide-7-methyl-ester 15: The foregoing formyl derivative 14 (mg) was reacted with osmium tetroxide (mg) by following the methodology as discussed for bacteriopurpurin X and the product (as diasteriomeric mixture) was isolated. $^1$H NMR (ppm): [mixture of two isomers, vic diols are cis- up and cis-down relative to the ring D].

2-Formyl-vic-dihydroxy bacteriopurpurin-N-hexylimide-7-aspartic acid di-tert-butyl ester 24: As shown in FIG. 5, for the preparation of the desired photosensitizer, the foregoing methyl ether analogue will be converted to corresponding carboxylic acid on reacting with aq. HCl. The carboxylic acid will be reacted with aspartic acid di-tert-butyl ester in presence of DCC and catalytic amount of DMAP, which on further reacting with osmium tetroxide/$H_2S$ will give the title bacteriopurpurin.

2-Formyl-vic-dihydroxy bacteriopurpurin-18, 7-methyl ester 7: 2-Formyl-purpurin-7 -methyl ester 4 (mg) was dissolved in dichloromethane (ml), osmium tetroxide (mg) dissolved in diethyl ether (ml) and pyridine (ml) was added and the reaction mixture was stirred in a sealed flask (by using a rubber septum). The reaction was monitored by analytical TLC and spectrophotometry (appearance of a peak at 825 nm, and disappearance of the starting material peak at 734 nm). The osmate ester so obtained by converted to diol by bubbling a slow stream of $H_2S$ gas through the solution. The reaction mixture was filtered, solvent was evaporated and the residue was purified by silica chromatography, eluting with 5% methanol in dichloromethane. The dark pink eluates were collected. After-evaporating the solvent, the residue was crystallized from $CH_2Cl_2$/hexane. $^1H$ NMR (ppm), 11.40 (s, CHO), 9.70, 9.20, 8.10 (each s, meso H), 5.16 (m, 7-H), 4.35 (m, 8-H), 3.50–3.70 (2 and 5 ring $CH_3$ and $CO_2CH_3$), 3.62 (m, $CH_2CH_2CO$), 3.20, 2.70 (each m, 4-$CH_2CH_3$, and 7-bCH), 2.40 and 2.42 (each s, 3H, 3-$CH_3$), 1.76 (2 d, merged, 6H, 2×8 $CH_3$), −0.10, −0.18, −0.30 and −0.42 (s, NH protons).

2-Formyl-vic-dihydroxy bacteriopurpurin-18, 7-aspartic acid-di-tert-butyl ester 10: 2-Formyl purpurin-18 6 (mg) was reacted with osmium tetroxide ( ) by following the methodology as discussed for the foregoing bacteriopurpurin and was obtained. NMR (ppm) {vis - diols are cis- up or cis- down relative to the ring D}: 11.35 (s, CHO), 9.65, 9.18, 8.08 (s, meso H), 6.60 and 6.45 (d, Asp-NH), 5.15 (m, 7-H), 4.62 (X Of ABX, Asp-CH), 4.35 (m, 8-H), 3.60, 3.61, 3.70 and 3.72 (s, $CH_3$), 3.60 ($CH_2$ of $CH_2CH_2CO$), 3.20, 2.50–3.00 (each m, 4-$CH_2CH_3$, 7b-CH, Asp-$CH_2$), 2.40 and 2.42 (each s, 3H, 3-$CH_3$), 1.74 (2d, merged, 3H, 8-$CH_3$), 1.40, 1.38 (each s, 9H, $CO_2Bu^t$), 1.18 and 0.8 (each t, 4-$CH_2CH_3$), −0.08, −0.18, −0.38 and −0.40 (each s, NH).

2-Formyl-vic-dihydroxy bacteriopurpurin-18, 7-aspartic acid dimethyl ester 8: 2-Formyl analogue 6 (mg) was reacted with osmium tetroxide/pyridine and then HS was bubbled to cleave the intermediate osmate as discussed for the preparation of other bacteriopurpurins and the product was isolated in % yield after purification by preparative plates (Silica Gel), eluting with 5% methanol/dichloromethane. $^1H$ NMR (ppm): the resonance for most of the protons were same as discussed for the foregoing bacteriochlorins, except the resonances for the tert-butyl groups were missing. The resonances for two —$CO_2CH_3$ were observed at 3.70 to 3.75 ppm.

2-Formyl-vic-dihydroxy bacteriopurpurin-N-lyseleloxy-imide-7-methyl ester 19: 2-Formyl-N-lyseleloxyimide-7-methyl ester 18 (mg) was reacted with osmium tetroxide on similar lines as discussed for the preparation of other bacteriopurpurin diols and was isolated, NMR (ppm) [vic- diols are cis- up or down, relative to the ring D] 11.25, 11.20 (each s, 1H, CHO), 9.52, 9.50, 9.15, 9.10, 8.62 and 8.60 (each s, 1H, meso H), 5.20–5.30 (m, 2H, 7-H), 4.49 (m, 6-lysine $CH_2$), 4.38 (m, 8 H), 4.20 (m, 6-lysine $CO_2CH_2$), 3.42–3.70 (six s. 3H, 1,5 ring $CH_3$ and 7-$CO_2CH_3$), 2.30, 2.20 (each s, 3H, 3-$CH_3$), 1.70 (2 d, each 3s, 8 CH3), 1.40 (t, $CH_2CH_3$), 0.80, 0.65 (each t, 3H, 4-$CH_2CH_3$), −0.45 and −0.55 (each s, NH).

Preparation of Bacteriopurpurin analogues with less hydrophilicity:

In recent years we have synthesized and evaluated a series of photosensitizers related to porphyrins, chlorins and bacteriochlorins, and have observed that the hydrophilicity/hydrophobicity plays an important role for an effective photosensitizer. Besides, those photosensitizers in which the hydrophilic groups are attached only at one half of the molecules were found to be more active than those in which these groups are present at both sides of the molecule. In order to achieve our objective, following two methods were used:

Method 1: In this approach, bacteriopurpurin 29 was obtained from bacteriochlorophyll-a 26, which in turn can be isolated from R. Spheroides or R. Capsulata. In brief, bacteriochlorophyll-a 26 (5 mg) [obtained from the Porphyrin products, Logan, Utah, U.S.A.] was dissolved in diethylether (20 ml). 25% KOH (aqueous) in i- propanol was added and the reaction mixture was stirred at room temperature for 1 h while the air was bubbled through it. Conc. HCl (5 ml) was added to the solution dropwise and the reaction mixture was stirred for another 0.5h. The reaction mixture was extracted with diethyl ether (3×50 ml), washed with water till the pH of the aqueous phase is neutral. The ethereal layer was dried over anhydrous sulfate, and treated with ethereal diazomethane to convert the carboxylic acid to corresponding methylester. After evaporating the solvent, the residue was chromatographed on silica, eluting with chloroformacetone as eluent. Evaporation of the solvent gave the desired bacteriopurpurin X in which the vic-dihydroxy groups are replaced with H substituents. Currently, efforts are being made to optimize the reaction conditions. max 361 ( ), 406 ( ), 540 ( ), 818 ( ). NMR ($CDCl_3$): 9.20, 8.80, 8.62 (each, meso H), 4.20 (7.8-H, m), 4.0 (3,4-H,m), 3.57, 3.47 (each s, 3H, $CH_3$), 3.15 (7b-H), 3.10 ($COCH_3$), 2.70 (7a-H, m), 2.26 (q, 2H, $CH_2CH_3$), 1.72(d,3H, 8-$CH_3$), 1.62 (d, 3H, 3-$CH_3$), 1.06 (m, 3H, $CH_3$), −0.38 (s, 1H, NH), −0.80 (s, 1H, NH).

Figure 6:
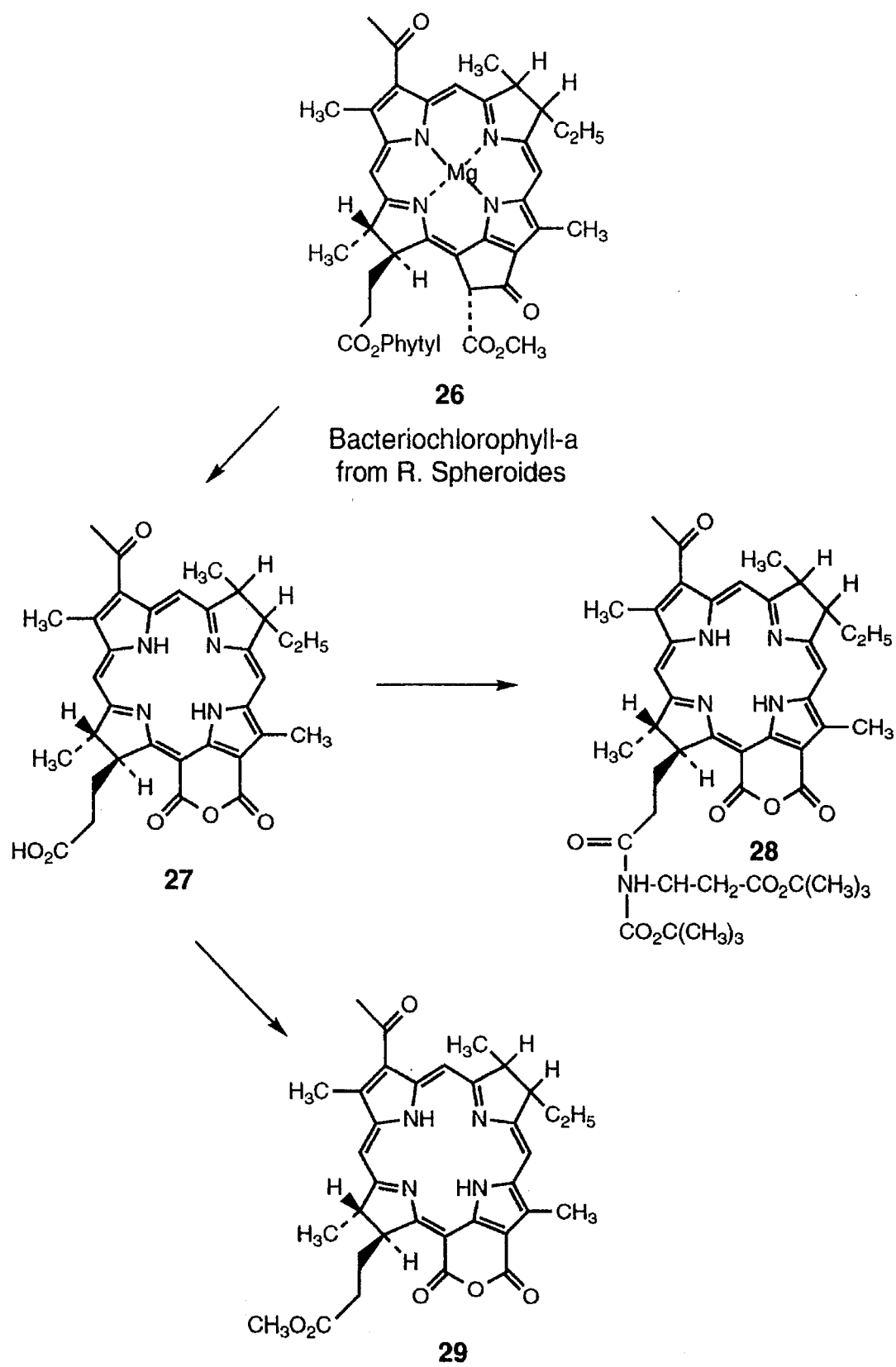
FIG. 6 is a schematic equation showing the synthetic route to compound 29.

For the preparation of aspartic acid derivatives 28, efforts are currently being made to react the intermediate carboxylic acid to aspartic acid di tert- butyl ester by following the methodology as described for the preparation of other such derivatives. See FIG. 6.

Method 2: In this approach, efforts are being made to convert the vic -dihydroxy groups in bacteriopurpurins, e.g., to corresponding alkyl ether derivatives, or respective keto bacteriopurpurins 30 and 31 respectively (FIG. 7), which will make these compounds more hydrophobic and presumably will retain in tumor for longer time.

Biological Results (in-vivo studies):

The new photosensitizers were screened in a mouse/tumor model system. A model system consisted observing the size reduction of the SMT-F tumor, a fast growing spontaneous mouse mammary tumor subline, transplanted subcutaneously to male or female DBA/2 HA-DD mice according to method described by Dougherty et al. The tumor line was maintained in vivo via serial transplantation in the same mouse strain. DBA/2 Ha-DD mice are readily available and were obtained locally.

When mice were both the appropriate age (approximately 6 weeks) and weight (approximately 20 g), small pieces of tumor (1–2 mm cube) were transplanted with a 18 gauge trocar from a donor tumor to recipient mouse. This technique provides for relatively uniform tumor size and allows location of the tumor in the right auxiliary region of the animal within each experimental group. Only animals with single tumors were chosen for experiments. When tumor reached 3–4 mm diameter, the animals were injected with the potential photosensitizer chosen from the group described above. Prior to irradiation, the fur overgrown and surrounding the tumor was removed with electric clippers. Three or twenty four hours after injecting the drug, the mouse was placed in a custom made aluminum holder.

Irradiation Conditions:

Standard light dose was 75 mW/cm for 30 min for a total incident light dose of 135J cm from a tunable dye laser tuned to the maximum red absorption peak. Spectra Physics 2040, a quartz fiber fitted with a microlens was interfaced to the dye laser deliver a uniform field of light. Laser output was measured with a power meter.

Experimental Procedure:

Following light exposure, the mice were kept in groups of 5 per cage and supplied with pelleted food and tap water ad libitum. Tumor size and gross appearance of both tumor and overlying surrounding skin was monitored daily for 80 days after photoillumination unless growth of non-responsive tumor require early sacrifice of those animals.

The photosensitizer was dissolved in known quantity of Tween-80 (Aldrich) surfactant and diluted by a factor of 10 with saline solution to produce a final Tween-80 concentration of 10%. The solution was then filtered through a syringe filter. The concentration of the solution was determined on the basis of the extinction coefficient value of the photosensitizer at the longest wavelength absorption. Absorption spectra were obtained using a Perkin Elmer 330 spectrophotometer.

Before injecting the drug into mice, the purity of the compounds was ascertained by analytical HPLC using Spectra Physics HPLC, connected with C8 reverse phase column, eluted with methanol/water by adjusting the pH to 7.0 using phosphate buffer.

TABLE 1

Comparative in vivo Activity of Some Bacteriochlorins*

| Compound | Dose mg/kg | Absorbance max | Time (h) between inj. and light treatment | % Tumor Response (days)** 1–2 | 7 | 21 | 30+ |
|---|---|---|---|---|---|---|---|
| 7 | 5.0 | 816 | 3.0 | 0 | — | — | — |
| 8 | 5.0 | 816 | 3.0 | 0 | — | — | — |
| 10 | 5.0 | 816 | 3.0 | 100 | 100 | 80 | 80 |
| 19 | 5.0 | 816 | 3.0 | 100 | 100 | 20 | 20 |

*4–6 mm diameter tumors were exposed to 75 MW/cm² for 30 min to deliver 135 J/cm² from a tunable dye laser tuned to the maximum red absorption peak
**Non palpable tumors

What is claimed is:

1. A compound comprising:

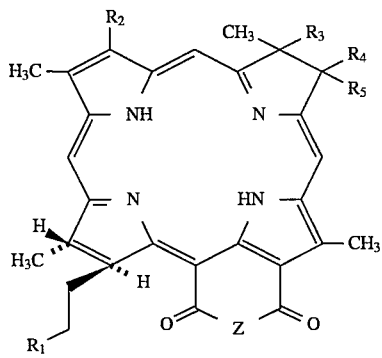

where z is $=O$ or $=NR_6$, where $R_6$ is lower alkyl of from 1 to 8 carbon atoms or

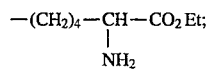

$R_1$ is

where $R_7$ is

or $—OR_8$, where $R_8$ is hydrogen or lower alkyl of 1 to 8 carbon atoms, or $R_7$ is an amino acid residue connected at a nitrogen atom of such residue; $R_2$ is lower alkyl or lower alkylene of from 2 to 4 carbon atoms or a formyl or carbonyl containing group of from 1 to 4 carbon atoms; $R_3$ and $R_4$ are $—H$ or $—OR_8$ and $R_4$ may be taken together with $R_5$ to form $=O$; and $R_5$ is ethyl or is taken together with $R_4$ to form $=O$; provided that when Z is $—O—$, the sum of the number of carbon atoms in, $R_1$ through $R_5$ is from 12 to 20 and when Z is $=NR_6$, the sum of the number of carbon atoms in $R_1$ through $R_6$ is 8 to 20.

2. The compound of claim 1 wherein Z is $=NR_6$ and $R_3$ and $R_4$ are $—OH$.

3. The compound of claim 1 wherein $R_3$ and $R_4$ are $—OH$.

4. The compound of claim 2 wherein Z is $=NR_6$ and $R_3$ and $R_4$ are $—H$.

5. The compound of claim 3 wherein $R_7$ is amino acid residue.

6. The compound of claim 4 wherein $R_6$ is

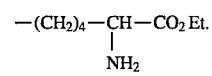

7. The compound of claim 1 wherein $R_2$ is $—CHO$; $R_3$ and $R_7$ are $—OH$ and $R_5$ is $C_2H_5$.

8. The compound of claim 7 wherein $R_1$ is $—CO_2Me$ and Z is $=N(CH_2)_5CH_3$.

9. The compound of claim 7 wherein $R_1$ is $—CO_2Me$ and Z is

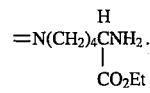

10. The compound of claim 7 wherein $R_1$ is $—COOH$ and Z is $=N(CH_2)_4 CH(CO_2Et)NH_2$.

11. The compound of claim 7 wherein $R_1$ is $—COOH$ and Z is $=N(CH_2)_5CH_3$.

12. The compound of claim 1 wherein $R_2$ is

and $R_3$ and $R_4$ are $—H$.

13. The compound of claim 12 wherein $R_1$ is $—COOCH_3$ and Z is $=O$.

14. The compound of claim 7 wherein $R_1$ is

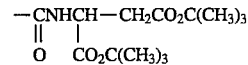

and Z is $=O$.

15. The compound of claim 12 wherein $R_1$ is

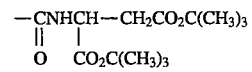

and Z is $=O$.

* * * * *